United States Patent [19]

Kübler

[11] Patent Number: 4,996,878
[45] Date of Patent: Mar. 5, 1991

[54] TRANSDUCER ELEMENT FOR MEASURING ANGULAR AND LINEAR ACCELERATION

[75] Inventor: John Kübler, E. Amherst, N.Y.

[73] Assignee: Kistler Instruments AG, Winterthur, Switzerland

[21] Appl. No.: 478,017

[22] Filed: Feb. 9, 1990

[30] Foreign Application Priority Data

Jan. 29, 1988 [EP] European Pat. Off. ......... 881013031

[51] Int. Cl.$^5$ .............................................. G01P 15/09
[52] U.S. Cl. .................................. 73/510; 73/517 A; 73/651
[58] Field of Search ................. 73/510, 517 R, 517 A, 73/651; 310/329

[56] References Cited

U.S. PATENT DOCUMENTS 4,038,876 8/1977 Morris ................................... 73/510
4,457,173 7/1984 Hunter .................................. 73/510

Primary Examiner—John Chapman
Attorney, Agent, or Firm—Barnes & Thornburg

[57] ABSTRACT

A transducer element for measuring angular and linear accelerations including a pair of electromechanically reacting oscillating beams held symmetrical to a main axis y on a base plate by fixing elements. The electrical output signals proportional to the flexure of the beams under rotation about the y axis are provided to a signal processing circuit, which is designed so that with similar or dissimilar polarity of the oscillating beams a summing amplifier determines the linear acceleration along the z axis and a differential amplifier the angular acceleration about the y axis. The oscillating beams may be piezoelectric bending elements, or bending elements coated with piezoresistive semiconductors, or else provided with strain gauges.

5 Claims, 2 Drawing Sheets

FIG. 3
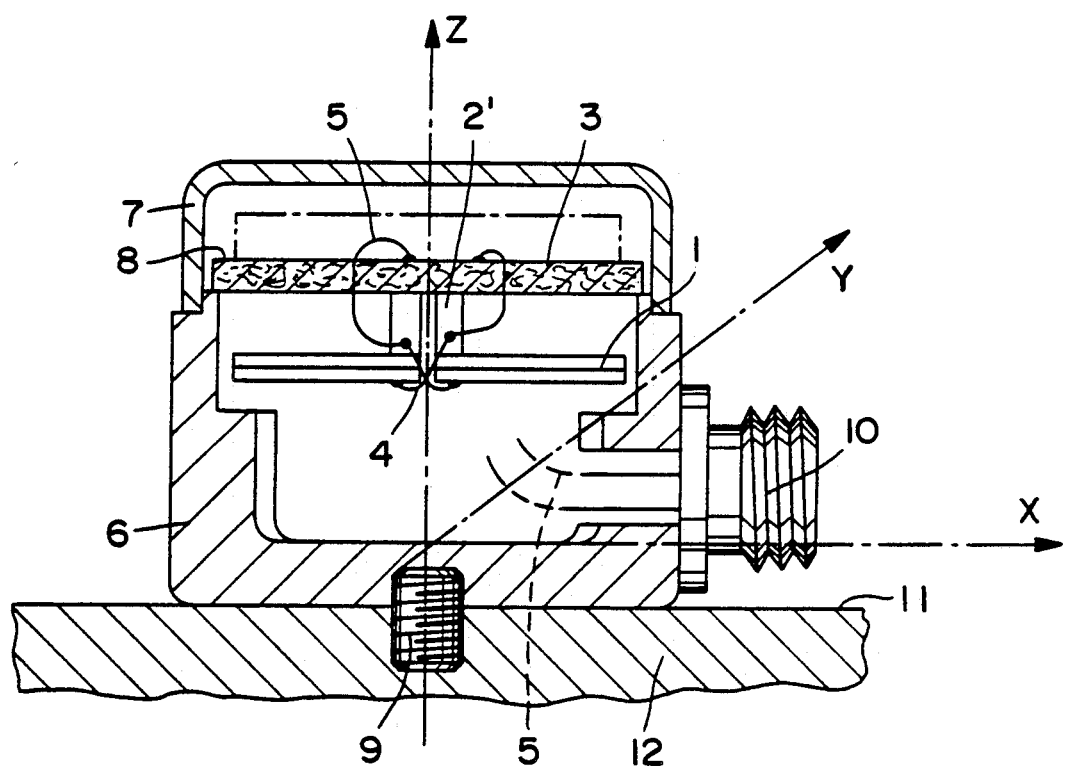
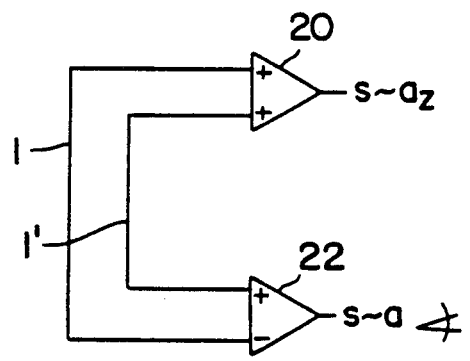
FIG. 4

TRANSDUCER ELEMENT FOR MEASURING ANGULAR AND LINEAR ACCELERATION

This is a continuation of application Ser. No. 07/286,728, filed Dec. 20, 1988, abandoned.

BACKGROUND AND SUMMARY OF THE INVENTION

The present invention relates generally to a transducer element for measuring angular and linear acceleration, and more specifically for use preferentially in modal testing and for measuring rotational acceleration on shafts, and an accelerometer equipped with it.

Knowledge of the vibration behavior of engineering structure is of fundamental importance in many domains. In view of its importance, analysis of the vibration behavior has recently acquired a special name: modal testing. It is partly experimental, partly theoretical in character. Its purpose is to obtain a mathematical model of the vibration behavior of a structure. The importance of this for turbine blades, but also for bridges, is obvious. Accelerometers are suitable instruments for analyzing vibration behavior. They measure accelerations that occur typically during vibration. Owing to the lack of suitable instruments, chiefly linear accelerations have hitherto been measured. This was done by joining the accelerometer rigidly to the surface of the object to be measured, either by screwing or gluing it. When vibrations occurred on the object, the accelerations could be measured by a conventional accelerometer of this kind typically at right angles to the surface, in one dimension that is. Also, two- or three-dimensional acceleration measurements were and still are used, by measuring the acceleration additionally in one or two directions at right angles to each other and parallel with the surface of the object to be tested. Nevertheless, linear accelerations have been measured previously for the most part. Yet, the theory of modal testing, as expounded for example in the book "Modal Testing, Theory and Practice" by D.E. Ewins, Research Study Press Ltd., 1984 on pages 87-152, indicates that angular accelerations are just as important as linear accelerations and that modal testing is incomplete without analyzing the angular accelerations.

In the book named, on pages 146 to 148, the principles of angular acceleration measurement are also set out, based on measurement of rotary impulses by registering acceleration with two accelerometers at a certain distance apart. In commercial printed matter, instruments are also described occasionally which serve to measure both linear and angular acceleration. The measurement of angular rate is described moreover in U.S. Pat. Nos. 2,716,893; 3,842,681 and 4,431,935. However, no instrument is described capable of measuring angular acceleration and linear acceleration together. Moreover, the accelerometers described have insufficient sensitivity and are too big and too heavy for modal testing.

It is therefore the purpose of the present invention to provide a transducer element or accelerometer of the kind mentioned at the beginning, allowing exact measurement of both angular and linear accelerations and particularly suitable for modal testing, though not solely for this.

The purpose is fulfilled by cantileverly mounting a pair of electromechanical beams to a main axis. The beams oscillate in response to vibrational acceleration of the object to which they are attached and thus will be called herein oscillating beams. When the beams are made of material having electrical polarization directions, they will be referred to as having electrical polarities. The electrical output signals, produced by the flexure, are provided to a signal processing facility, which adds the output signals if the electrical polarity of the oscillating beams is dissimilar and subtracts them if the polarity is the same to generate a characterizing measuring signal for the angular acceleration about the main axis. By reversing the operations, linear instead of angular acceleration may be measured. A signal processing facility allows simultaneous measurement of both angular and linear acceleration. The transducer element is of simple and rugged construction, permitting each miniaturization for the requirements of modal testing. Thus, both angular and linear accelerations can be detected with one and the same transducer element. According to a further development of the invention, the oscillating beams are mounted preferably by fixing elements on a base plate joinable with a housing. The oscillating beams may be piezoelectric bending elements, bending elements coated with piezoresistive semiconductor material, or bending elements provided with strain gauges. The electronic equipment may be integrated wholly or partly in the transducer element. Furthermore, the invention creates an accelerometer for measuring angular and/or linear acceleration, featuring a housing in which at least one transducer element is allotted preferably to each of the three main axes, for detecting the angular and/or linear accelerations in the three coordinate directions.

Other objects, advantages and novel features of the present invention will become apparent from the following detailed description of the invention when considered in conjunction with the accompanying drawings.

BRIEF DESCRIPTION OF THE DRAWINGS

FIG. 3 is a cross-sectional view of an accelerometer incorporating a transducer element according to the invention for measuring angular acceleration; and FIG. 4 is a block diagram of a signal processing facility.

DETAILED DESCRIPTION OF THE DRAWINGS

Figure 1:
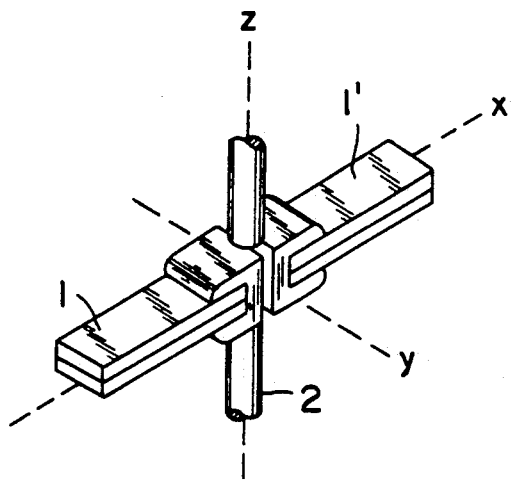
FIG. 1 is a perspective view of a transducer element constructed according to the principles of the present invention.

As shown in FIG. 1, the transducer element comprises a pair of oscillating beams 1 arranged on either side of a rigid shaft 2. The oscillating beams are identical in shape and have much greater expansion in the longitudinal and lateral directions than in the direction of the thickness. The oscillating beams 1 extend symmetrically at both sides of and in relation to a system axis Y, and lie at rest in a plane defined by the axes x, y at right angles to the central axis z of the system.

If the housing (not shown) of an accelerometer joined rigidly to the measuring object sustains an upward acceleration in the z direction for example, this acceleration acts through the rigid shaft 2 onto the oscillating beams 1, which owing to their elasticity bend down under the effect of the inertia forces. Conversely, the oscillating beams 1 bend up if the acceleration is directed downward. On the other hand, accelerations in the x and y directions, i.e., in the plane of the oscillating beams, cause no deformation of the oscillating beams 1 essentially, because these are much stiffer in both the x and y directions than in the z direction. Besides linear accelerations in the z direction, angular accelerations of the transducer element about the x axis also cause flexure of the oscillating beams, as is explained later in connection with FIG. 2b. The flexures of the oscillating beams due to the accelerations are registered by metrological means and evaluated.

The function of a transducer element for measuring angular and linear accelerations will now be explained with reference to the preferred design of the oscillating beams 1 in the form of piezoelectric bimorph elements exploiting the transverse effect preferentially. Needless to say, the invention is not restricted to this, but may embody other electromechanically reacting oscillating beams also, for example in the form of bending elements coated with piezoresistive semiconductor material. Also strain gauges fixed on the oscillating beams may be employed to detect the flexure.

Piezoelectric bimorph elements are known to persons skilled in the art and have been described for example in "Piezoelektrische Messtechnik" by J. Tichy and G. Gautschi, published by Springer Verlag, 1980, page 149.

Figure 2B:
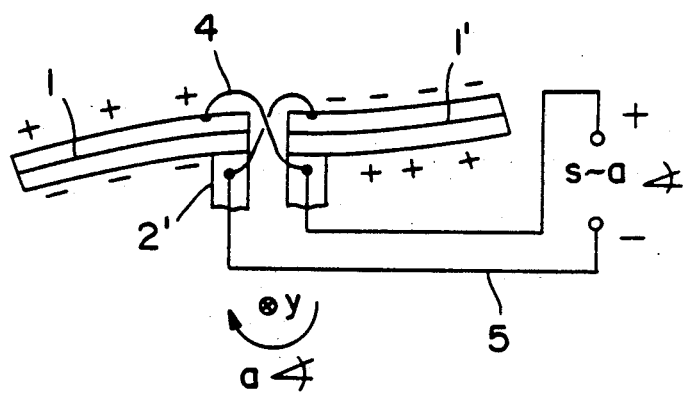
FIGS. 2a-2b are schematic views of the circuitry employed to eliminate angular acceleration when measuring the linear acceleration (FIG. 2a), or eliminate the linear acceleration when measuring angular acceleration (FIG. 2b)
Figure 2A:
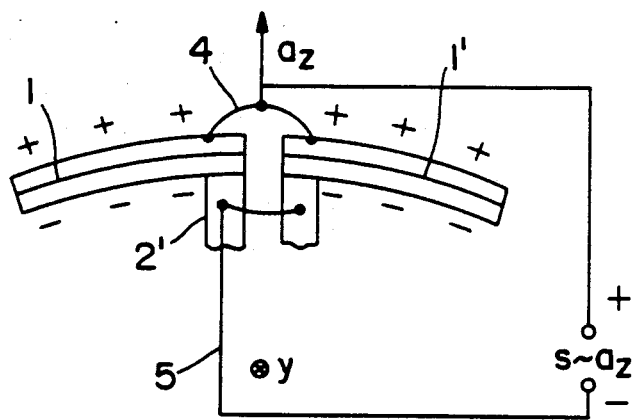

FIGS. 2a and 2b show the signal generation and evaluation schematically, using the piezoelectric bimorph beam element as an example. If a beam is bent down, it is stressed in tension above the neutral layer and in compression below this. Positive charges are then set up typically in the upper side of the beam and negative charges in the lower side. Electrical contacts are attached to the upper and lower side. Attached to these electrical contacts are either connecting lines 4 for interconnecting the piezoelectric elements, or signal lines 5 serving to lead off the signals, to charge amplifiers (not shown) for example. The two oscillating beams 1 are separated electrically and fixed typically to the base disk 3 not shown here (shown in FIG. 3) by the beams mountings 2'. The beam mountings 2', or at least part of them, are assumed to be electrically conductive in FIGS. 2a and 2b.

The polarity of the beam 1 shown in FIG. 2a is such that a downward flexure sets up positive charges on the upper side and negative charges on the underside. An acceleration $a_z$ in the z direction, i.e., at right angles to the two beams, induces the same downward flexure in each beam.

If, as shown in FIG. 2a the contact points (not shown) on the undersides of the beams are short-circuited, and those on the upper side also, and the corresponding signals are led off by signal lines 5, the resulting signal s is a measure for the linear acceleration $a_z$ along the axis z (i.e., s is proportional to $a_z$) over a wide range.

FIG. 2b shows the circuitry for measuring angular acceleration. The beam type used is the same as in FIG. 2a. If an angular acceleration "a" occurs clockwise, as indicated, the beam on the left side bends down and that on the right side bends up. As in FIG. 2a, consequently positive charges occur on the top of the left-hand beam and negative charges on the bottom. On the right-hand beam, positive charges occur on the bottom and negative ones above, because the curvature is reversed. If the contact point on the upper side of the left-hand beam is connected with that on the underside of the right-hand beam and vice versa (connecting lines 4), the resulting signal s led off from the lower contact points via the signal lines 5 is a measure for the angular acceleration "a" (i.e., s is proportional to a) over a wide range.

If the same circuitry as in FIG. 2a were used when measuring the angular acceleration (FIG. 2b), the output signal s would be zero. This shows that when measuring the linear acceleration according to FIG. 2a, the influence of any angular acceleration occurring at the same time is eliminated. Analogous reasoning leads to the conclusion that when measuring angular acceleration with the circuitry shown in FIG. 2b, the influence of linear acceleration is eliminated. This is based on the assumption that both beams consist of piezoelectric material, whose electrical polarization direction has the same orientation ("same electrical polarity"). If, for example, with the beams shown in FIG. 2a the right-hand one had inverse orientation ("dissimilar electrical polarity"), at the downward bending negative charges would occur on the upper side and positive ones on the underside. Now in order to enable the linear acceleration to be measured, the contact points on the lower and upper sides respectively should not be short-circuited as shown in FIG. 2a; instead the crosswise circuitry shown in FIG. 2b ought to be employed. The same is true by analogy of measuring angular acceleration. With "dissimilar electrical polarity" of the beams on the left- and right-hand sides, the circuitry in FIG. 2a should be used and not the crosswise circuitry of FIG. 2b. The manner in which the polarization directions shown in the figures may result will not be explained further here, since it is no subject of the invention. It may be mentioned also that the beams do not have to be two-part, bimorph. They could also be in more parts, as shown for example in U.S. Pat. No. 4,431,935.

The four contact points for the top and bottom of 1 and 1' shown in FIGS. 2a and 2b can be connected with a signal processing facility containing a summing amplifier 20 and a differential (operational) amplifier 22. As illustrated in FIG. 4, the summing amplifier 20 then delivers an output signal proportional to the linear acceleration, and the differential amplifier 22 a signal proportional to the angular acceleration. With this circuitry, it is possible to measure angular and linear acceleration simultaneously with a single transducer element having two beams. Measurements in modal analysis are simplified and speeded-up in this way, opening up new application possibilities furthermore.

FIG. 3 shows a cross section through an accelerometer according to the invention for measuring angular acceleration about an axis y parallel with the surface 11 of the measuring object 12 and at right angles to the plane of the drawing. The reference numbers used in the previous figures have the same meanings here. The measuring system consisting of base disk 3, fixing elements 2 and oscillating beam 1 is joined rigidly to a transducer body consisting of a solid housing base body 6 and a housing cover 7. The signals are taken from the contact points (not shown) on the base disk 3 via the lines 5 (shown with broken lines) and out through a plug and socket connection 10. Into this socket 10 a low-noise cable with high impedance (not shown) may be plugged in conventional manner, leading to an external electronic signal evaluation unit. However, this electronic signal evaluation may also be integrated in the transducer body by mounting the necessary electronic components, such as operational amplifier and charge amplifier, on the base disk 3 for example as illustrated by the phantom lines in FIG. 3. This integration of the electronics eliminates problems that may arise in the signal transmission by high-impedance cable. What is important is that the vibrations of the measuring object 12 are transmitted without falsification via the transducer body 6, 7 and the stage 8 onto the transducer element. To ensure this, the accelerometer must be joined rigidly to the surface 11 of the measuring object 12, which is usually accomplished with a fixing screw 9. A firm glued joint between the accelerometer and the surface named is also possible. With appropriate design of the signal processing unit described above, the accelerometer shown in FIG. 3 can be used to measure simultaneously the angular acceleration about an axis y parallel to the surface 11 of the measuring object 12 and the linear acceleration along the z axis at right angles to this.

By providing several transducer elements of this kind, so that all three coordinate axes at right angles to each other are covered, it is possible to construct an accelerometer for measuring the angular accelerations about each of the axes x, y and z. At the same time, by extending the signal processing facility as already described, the linear accelerations acting along the axes x, y and z can be registered in addition. Thus, the invention brings small and lightweight transducer element or accelerometer of simple construction, which allows a clear-cut separation of angular and linear accelerations and is especially suited for modal testing.

The embodiment of an accelerometer according to the invention shown in FIGS. 2a, 2b and 3 can be used also to measure the angular accelerations on shafts. The oscillating beams 1 are then placed on a circular disk by the fixing elements 2. This circular disk is fixed in a housing which is mounted rigidly on the shaft to be measured. The axis of the shaft and the center of the circular disk define the system axis, to which the oscillating beams 1 lie symmetrical. The shaft to be tested is set in motion by a motor. If the signals are exploited analogously to FIG. 2b, in this way the mean angular acceleration about the system axis can be determined for example. But also the angular acceleration in a distinct angular position can be measured using an oscilloscope or a plotter for instance.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. Transducer element for measuring angular and linear acceleration comprising:
   a pair of electromechanical beams extending along a first axis in a common plane and cantileverly mounted to at least one fixing element substantially at a second axis perpendicular to said plane of said beams and symmetrical with respect to a third axis orthogonal to said first and second axis;
   means for fixedly mounting said fixing element to an object whose angular acceleration about said third axis and linear acceleration along said second axis are to be measured;
   each of said beams comprising piezoelectric material having a specific electrical polarization direction;
   first means for connecting electrical output signals generated by the flexure of the beams to a signal processing facility as a sum of the output signals if the material of the beams have different electrical polarization directions and as a difference of the output signals if the electrical polarization directions are the same, to produce a measuring signal representing the angular acceleration of the object about the third axis; and
   second means for connecting said output signals to a signal processing facility as a sum of the output signals from the beams if the material of the beams have the same electrical polarization directions and as a difference of the output signal if the electrical polarization directions are dissimilar, to produce a measuring signal for the linear acceleration along said second axis at right angles to the plane of the beams.

2. Transducer element according to claim 1, wherein said first means includes conductors connecting terminals of said beams in addition if said material of said beams have different electrical polarization directions and in subtraction if said material of said beams have the same electrical polarization directions; and
   said second means includes conductors connecting said terminal of said beams in subtraction if said material of said beams have different electrical polarization directions and in addition if said material of said beams means have the same electrical polarization directions.

3. Transducer element according to claim 1, wherein said first means includes a difference amplifier connected to different polarity terminals of said beams if said material of said beams have different electrical polarization directions and to same polarity terminals of said beams if said material of said beams have the same electrical polarization directions; and
   wherein said second means includes a summing amplifier connected to different polarity terminals if said material of said beams have different electrical polarization directions and to same polarity terminals if said material of said beams have the same electrical polarization directions.

4. Transducer element according to claim 1, wherein said fixing element is fixedly mounted to a base plate joinable to a housing.

5. An accelerometer for measuring angular and linear acceleration comprising:
   a housing having first, second and third orthogonal axes;
   at least one transducer element having a pair of electromechanical beams extending along said first axis in a common plane and cantileverly mounted to at least one fixing element substantially at said second axis perpendicular to said plane of said beams and symmetrical with respect to said third axis orthogonal to said first and second axis, each of said beams comprising piezoelectric material having a specific electrical polarization direction;
   means for fixedly mounting said fixing element to said housing along said second axis;
   means for fixedly mounting said housing to an object whose angular acceleration about said third axis and linear acceleration about said second axis are to be measured; and signal processing means in said housing for receiving electrical output signal generated by the flexure of the beams, for adding said output signals if the material of the beams have different electrical polarization directions and subtracting the output signals if the electrical polarization directions are the same to produce an angular acceleration measuring signal about said third axis, and for adding said output signals if the material of said beams have the same electrical polarization directions and subtracting said output signals if the electrical polarization directions are different to produce a linear acceleration measuring signal along said second axis.

* * * * *